(12) United States Patent
Cheng et al.

(10) Patent No.: US 7,678,958 B2
(45) Date of Patent: Mar. 16, 2010

(54) METHOD OF REMOVING DIMETHYL ETHER FROM AN OLEFIN STREAM

(75) Inventors: Minquan Cheng, Evansville, IN (US);
Jeffrey J. Phillips, Houston, TX (US);
Michael Peter Nicoletti, Houston, TX (US); David Ritchie Lumgair, Jr., Craddockville, VA (US); John Richard Shutt, Tervuren (BE); Jeffrey Alan Kabin, Houston, TX (US); Wilfried Borgmann, Baierbrunn (DE); Josef Kunkel, Bauting (DE); Helmut Fritz, Munich (DE); Roland Walzi, Feldafing (DE); Gerhard Lauermann, Bad Tolz (DE); Klaus Muller, Kirchseeon (DE)

(73) Assignee: ExxonMobil Chemical Patents Inc, Houston, TX (US)

( * ) Notice: Subject to any disclaimer, the term of this patent is extended or adjusted under 35 U.S.C. 154(b) by 1225 days.

(21) Appl. No.: 10/511,241

(22) PCT Filed: Sep. 30, 2002

(86) PCT No.: PCT/US02/31046

§ 371 (c)(1),
(2), (4) Date: Sep. 7, 2005

(87) PCT Pub. No.: WO03/033441

PCT Pub. Date: Apr. 24, 2003

(65) Prior Publication Data

US 2006/0111601 A1    May 25, 2006

Related U.S. Application Data

(60) Provisional application No. 60/345,666, filed on Dec. 31, 2001.

(30) Foreign Application Priority Data

Oct. 16, 2002    (DE) ................................. 101 50 479

(51) Int. Cl.
*C07C 7/04* (2006.01)
*C07C 1/207* (2006.01)

(52) U.S. Cl. .................. 585/809; 585/804; 585/638; 585/820; 585/639

(58) Field of Classification Search ................. None
See application file for complete search history.

(56) References Cited

U.S. PATENT DOCUMENTS 2,456,584 A * 12/1948 Gorin et al. ................. 585/408
6,121,504 A *  9/2000 Kuechler et al. ............ 585/640

\* cited by examiner

*Primary Examiner*—Tam M Nguyen
(74) *Attorney, Agent, or Firm*—Kevin M. Faulkner; Frank E. Reid (57) ABSTRACT

This invention is directed to a method of removing dimethyl ether from an olefin stream. The method includes distilling the olefin stream so that the dimethyl ether is separated out of the olefin stream with propane. The olefin stream can then be further distilled to provide a polymer grade ethylene stream and a polymer grade propylene stream, with each stream containing not greater than about 10 wppm dimethyl ether.

30 Claims, 6 Drawing Sheets

METHOD OF REMOVING DIMETHYL ETHER FROM AN OLEFIN STREAM

This application claims priority to German Patent Application No. 101 50 479.9, filed Oct. 16, 2001, U.S. Ser. No. 60/345,666, filed Dec. 31, 2001, and U.S. Ser. No. 10/196,530, filed Jul. 15, 2002, the descriptions of each being fully incorporated herein by reference.

FIELD OF THE INVENTION

This invention relates to removing dimethyl ether from an olefin stream. In particular, this invention relates to removing dimethyl ether from an olefin stream by distillation to form polymer grade ethylene and polymer grade propylene streams.

BACKGROUND OF THE INVENTION

Olefins, particularly $C_2$ and $C_3$ olefins, are desirable as a feed source for making derivative products such as oligomers, e.g., higher olefins, and polymers such as polyethylene and polypropylene. Olefin feed sources have traditionally been produced by cracking petroleum feedstocks.

U.S. Pat. No. 5,090,977 discloses a method of making olefins by steam cracking. The method includes separating the olefin product into methane, hydrogen, ethane, ethylene, propylene and $C_5+$ streams. The disclosed separation preferentially produces propylene, and no propane, butane, butene, or butadiene streams are produced.

Oxygenate feed stocks, however, are becoming an alternative to petroleum feed stocks for making olefins, particularly large quantities of ethylene and propylene for the production of higher olefins and plastic materials. In general, the olefins are formed by contacting the oxygenate components with a molecular sieve catalyst to catalytically convert the oxygenates to olefins. Such processes operate, for example, catalytically according to the overall equation $2CH_3OH \rightarrow C_2H_4 + 2H_2O$.

For example, U.S. Pat. No. 4,499,327, discloses a process for making olefins from methanol using any of a variety of silicoaluminophosphate (SAPO) molecular sieve catalysts. The process is carried out at a temperature between 300° C. and 500° C., a pressure between 0.1 atmosphere to 100 atmospheres, and a weight hourly space velocity (WHSV) of between 0.1 and 40 $hr^{-1}$. The process is highly selective for making ethylene and propylene.

U.S. Pat. No. 6,121,504 also discloses a method of making olefin product from oxygenate feed using molecular sieve catalysts. Water and other unwanted by-products are removed from the olefin product by contacting with a quench medium. After contacting with the quench medium, a light product fraction is obtained which comprises the desired olefins, but also includes dimethyl ether, methane, CO, $CO_2$, ethane, propane, and other minor components such as water and unreacted oxygenate feedstock.

One of the more particularly undesired by-products is dimethyl ether. The problem of removing dimethyl ether from an olefin product stream has not been satisfactorily solved up to now. Special absorber materials that are supposed to remove the dimethyl ether from the product stream have already been considered. However, it is difficult to find a suitable absorber or adsorber material for this purpose.

It is often necessary to reduce or remove the amount of undesirable hydrocarbon by-products that are present in the olefin composition in order to further process the olefins, particularly the ethylene, propylene and butylene. This is because derivative manufacturing processes may use catalysts that are quite sensitive to the presence of certain hydrocarbons. For example, the undesirable by-product dimethyl ether has been found to act as a poison to certain catalysts that are used to convert ethylene, propylene or butylene to other products.

U.S. Pat. No. 4,474,647 discloses, for example, that dimethyl ether can adversely impact the oligomerization of certain olefins. The patent describes a process for removing dimethyl ether from a $C_4$ and/or $C_5$ olefin stream using distillation. The stream is distilled and separated into an overhead and a bottoms stream. The overhead stream contains dimethyl ether, water, and various hydrocarbons, and the bottoms stream contains purified olefins.

U.S. Pat. No. 5,609,734 discloses a method of removing methanol and dimethyl ether from a mixed hydrocarbon stream. The hydrocarbon stream containing the methanol and dimethyl ether is distilled such that the dimethyl ether and methanol are removed in an overhead stream. Additional methanol is recovered in a side stream in which a methanol permeable membrane is used to obtain the additional separation. Purified hydrocarbon is removed from a bottoms stream.

Removal of dimethyl ether from olefin streams is particularly difficult, since very low levels of dimethyl ether can act as catalyst poisons. This means olefin streams such as $C_2$-$C_4$ olefins should contain little if any dimethyl ether, if further catalytic processing of the olefin stream is desired. Therefore, it is highly desirable to find additional methods of removing dimethyl ether from olefin streams.

SUMMARY OF THE INVENTION

This invention provides a method for removing dimethyl ether from olefin streams. The result of the method is that separate olefin streams, particularly ethylene, propylene, and butylene streams, can be obtained that are substantially reduced in dimethyl ether content.

The dimethyl ether is separated from the olefin product stream in this invention in a novel, yet economical, way. In one embodiment, the invention provides a method for removing dimethyl ether from an olefin-containing stream which includes fractionating the olefin-containing stream. The olefin-containing stream comprises a $C_3$ hydrocarbon stream and dimethyl ether, and the olefin-containing stream is fractionated to separate out the $C_3$ hydrocarbon stream, along with the dimethyl ether, from the olefin-containing stream. The $C_3$ hydrocarbon stream containing the dimethyl ether is then sent to a rectification column. Propylene is removed from a top portion of the rectification column, and propane is removed from a bottom portion of the rectification column. The dimethyl ether is also removed from the bottom portion of the rectification column along with the propane.

In another embodiment, the invention provides a method of separating dimethyl ether from an olefin stream made from an oxygenate to olefin reaction process. The method comprises contacting oxygenate with a molecular sieve catalyst to form the olefin stream. The olefin stream comprises, inter alia, water, propylene, propane, and dimethyl ether. The olefin stream is dried and distilled to separate the dimethyl ether and propane from the propylene.

In this invention it is desirable that the dried olefin stream contains not greater than about 1,000 wppm water. Preferably, the dried olefin stream contains not greater than about 500 wppm water; more preferably the dried olefin stream contains not greater than about 10 wppm water.

In one embodiment, the propylene distilled from the dried olefin stream is substantially free of dimethyl ether. Preferably, the propylene distilled from the dried olefin stream contains not greater than about 25 wppm dimethyl ether.

In another embodiment, the olefin stream contains at least about 0.05 wt % dimethyl ether. In yet another embodiment, the olefin stream further comprises butylene and higher boiling point compounds and the dried olefin stream is distilled to separate the dimethyl ether and propane from the propylene, butylene and higher boiling point compounds. In such an embodiment, the olefin stream desirably comprises from about 2 wt % to 45 wt % propane, from about 0.05 to about 5 wt % dimethyl ether, and from about 30 wt % to about 95 wt % butylene plus higher boiling point compounds.

The invention can further comprise contacting the propane and dimethyl ether with water to separate the dimethyl ether from the propane. The separated dimethyl ether can then be contacted with a molecular sieve catalyst to form an olefin.

Optionally, the invention further comprises polymerizing the separated propylene to form polypropylene. In addition, any butylene and higher boiling point compounds can be separated from the propylene, and the butylene can be further reacted. For example, the separated butylene can be converted into aldehydes, acids, alcohols, esters made from $C_5$-$C_{13}$ mono carboxylic acids and $C_5$-$C_{13}$ mono alcohols or linear alpha olefins.

In another embodiment of the invention, the olefin stream further comprises ethylene and the dried olefin stream is distilled to separate the dimethyl ether and propane from the ethylene and propylene. The separated ethylene can be polymerized if desired.

The invention further provides a method of removing dimethyl ether from an olefin stream in which the olefin stream comprises water, propylene, propane and dimethyl ether. The olefin stream is dried and distilled so as to separate out the propane and dimethyl ether from the propylene. In such an embodiment, it is preferred that the propane and dimethyl ether stream comprises from about 4.0 to about 99 wt % propane and from about 1.0 to about 96 wt % dimethyl ether, depending upon extent of conversion of oxygenate.

In another embodiment of the invention, olefin stream is dried by contacting the olefin stream with water absorbent or water adsorbent. The water absorbent is desirably a polar hydrocarbon. The water adsorbent is desirably a molecular sieve. It is also desirable to compress the olefin stream prior to contacting with water absorbent or adsorbent.

The invention further provides a method of polymerizing propylene made from an oxygenate. The method comprises contacting the oxygenate with a molecular sieve catalyst to form an olefin stream, wherein the olefin stream comprises propylene, propane, and dimethyl ether, the olefin stream is distilled to separate the propylene from the propane and dimethyl ether and the separated propylene is polymerized. Preferably, the separated propylene stream contains not greater than about 25 wppm dimethyl ether. It is also desirable to dry the olefin stream prior to distilling.

The invention further provides a method of polymerizing ethylene and propylene. The method comprises drying an olefin stream which comprises, inter alia, ethylene, propylene, propane and dimethyl ether. The dried olefin stream is distilled to separate out an ethylene stream, a propylene stream, and a propane and dimethyl ether stream such that the ethylene stream and the propylene stream each contain not greater than about 10 wppm dimethyl ether. The separated ethylene and propylene streams can then be polymerized. Preferably, the dried olefin stream contains not greater than about 1,000 wppm water.

BRIEF DESCRIPTION OF THE DRAWINGS

Examples of various embodiments of this invention are shown in the attached Figures, wherein.

DETAILED DESCRIPTION OF THE INVENTION

This invention provides a method of removing dimethyl ether from an olefin stream, particularly an olefin stream containing ethylene and/or propylene. In general, the method comprises distilling the olefin stream so as to separate out the propane and dimethyl ether in a common stream. The ethylene and/or propylene in the distilled olefin stream is of sufficient quality, i.e., polymer grade quality, to use as feed for a polymerization process.

The invention offers the advantage that no additional devices are needed for separating the dimethyl ether from the propylene product stream. A $C_3$ splitter that would be conventionally used to separate propane from the propylene can also be used to separate the undesirable dimethyl ether from the propylene.

In another aspect of the invention, the problem of removing dimethyl ether from an olefin stream is solved in accordance with the invention by separating at least a partial stream largely containing $C_3$ hydrocarbons from an olefin product stream by fractionation. The separated stream containing the $C_3$ hydrocarbons is sent to a rectification column ($C_3$ splitter) for separation of propylene and propane. A propylene product stream is taken from the top of this rectification column; and propane, and possibly other $C_3$ hydrocarbons, as well as dimethyl ether, are removed from the bottom portion of the rectification column so that a propylene product stream containing at most only traces of dimethyl ether is obtained.

Another aspect of the invention is based on fractionating the olefin stream so that dimethyl ether follows with the $C_3$ hydrocarbons in the separation process. Thus, dimethyl ether is sent with propylene, propane, and possibly other $C_3$ hydrocarbons, to a $C_3$ splitter or rectification column in the fractionation process. Surprisingly, it has now been found that the dimethyl ether goes nearly completely into the bottom portion of the rectification column along with the propane. The propylene is taken from the top portion of the column, and is substantially free of dimethyl ether.

In yet another aspect of this invention, it is desirable to distill an olefin stream that is low in water content in order to separate out the propane and dimethyl ether. A low water content will tend to avoid problems of clathrate and/or free water formation in the distillation vessel. Clathrates and free water formation can significantly impede heat and mass transfer, making it extremely difficult to separate products having relatively close boiling points. In some instances, the water content of the olefin stream may need to be reduced by drying the olefin stream in order to substantially reduce the effects of clathrate and free water formation.

The olefin stream that is to be distilled to separate out the dimethyl ether desirably contains not greater than about 1000 wppm water. Preferably the olefin stream contains not greater than about 500 wppm water, more preferably not greater than about 100 wppm water, and most preferably not greater than about 10 wppm water.

The method of this invention is particularly useful for removing dimethyl ether from ethylene and/or propylene streams which also contain propane. By distilling such a stream at a pressure and temperature effective to separate out dimethyl ether along with the propane, the result of the method is that the remaining portion of the olefin stream can be further distilled to provide polymer grade ethylene and polymer grade propylene feed streams, each being produced at high overall efficiency.

According to this invention, ethylene and/or propylene streams which contain propane and dimethyl ether can be obtained from any source. Some sources, however, will contain more of one component than another. For example, cracking various hydrocarbon materials will form ethylene and propylene, but little if any dimethyl ether, depending upon the material cracked. Converting oxygenates such as methanol to olefins by catalytic reaction with molecular sieve catalysts will also form ethylene and propylene, but significantly more dimethyl ether than cracking hydrocarbons. Nevertheless, as long as an olefin stream contains propane and dimethyl ether, the method of this invention will be effective. It is particularly effective, however, in removing dimethyl ether from olefin streams made from an oxygenate to olefin process, due to the relatively high content of dimethyl ether found in such streams.

In one embodiment of this invention, an olefin stream is provided which contains ethylene and/or propylene, dimethyl ether and propane. Optionally, the stream contains ethane, as well as butylene and higher boiling point compounds. The olefin stream is distilled, preferably by conventional continuous distillation techniques, so as to separate the ethylene and/or propylene, and optionally ethane if present, from the propane and dimethyl ether. If butylene and higher boiling point compounds are included in the olefin stream, it is preferred that the separated propane and dimethyl ether stream include the butylene and higher boiling point compounds.

In another embodiment of the invention, an olefin stream is provided which comprises from about 2 wt % to about 45 wt % propane. Preferably, the olefin stream comprises from about 5 wt % to about 40 wt % propane, and more preferably from about 10 wt % to about 35 wt % propane.

The provided olefin stream also contains dimethyl ether; desirably at least about 0.05 wt %. Preferably, the provided olefin stream contains from about 0.05 wt % to about 5 wt % dimethyl ether; more preferably from about 0.1 wt % to about 3 wt % dimethyl ether; and most preferably from about 0.2 wt % to about 2 wt % dimethyl ether.

Optionally, the provided stream comprises butylene plus higher boiling point compounds. This stream is typically present when the propane and dimethyl ether have been separated from an olefin stream containing a variety of $C_2$ and higher boiling point olefins. In this embodiment, propylene and lower boiling point compounds are removed from an olefin stream comprising $C_2$ and higher boiling point olefins by distillation.

The amount of butylene plus higher boiling point compounds which can be included in the provided olefin stream can vary depending upon the ultimate source of the olefin. In cases where the olefin stream includes ethylene and propylene, the butylene and higher boiling point materials are in a lower concentration. In cases where the ethylene and propylene have been separated from the olefin source, the butylene and higher boiling point compounds are in a higher concentration. In general, the provided olefin stream includes from about 30 wt % to about 95 wt % butylene plus higher boiling point compounds. Preferably, in this embodiment, the provided olefin stream has been previously distilled to remove ethylene and propylene, and the provided stream contains from about 40 wt % to about 95 wt % butylene plus higher boiling point compounds; more preferably from about 50 wt % to about 90 wt % butylene plus higher boiling point compounds; and most preferably from about 60 wt % to about 80 wt % butylene plus higher boiling point compounds.

In another embodiment of this invention, the dimethyl ether is separated from the propane stream by contacting the propane and dimethyl ether stream with water, preferably in the liquid phase. Contact can be performed in any conventional type of wash or liquid/liquid contact vessel The amount of water used should be sufficient to recover a propane stream containing at least about 85 wt % propane, preferably at least about 90 wt % propane, more preferably at least about 95 wt % propane.

The water stream that contacts the dimethyl ether and propane stream will absorb a substantial amount of the dimethyl ether. The water stream will be recovered as a bottoms stream from the contact vessel and contain at least about 1 wt % dimethyl ether, preferably at least about 3 wt % dimethyl ether, more preferably at least about 5 wt % dimethyl ether. The dimethyl ether can be separated from the water by vaporization, preferably by flash vaporization where the pressure is reduced to vaporize the dimethyl ether so that it can be easily separated from the water. The separated dimethyl ether can then be processed as desired. For example, the recovered dimethyl ether can be used as feed for the oxygenate to olefin reaction process.

In one embodiment of the invention, an olefin stream is obtained by contacting oxygenate with a molecular sieve catalyst. The oxygenate comprises at least one organic compound which contains at least one oxygen atom, such as aliphatic alcohols, ethers, carbonyl compounds (aldehydes, ketones, carboxylic acids, carbonates, esters and the like). When the oxygenate is an alcohol, the alcohol includes an aliphatic moiety having from 1 to 10 carbon atoms, more preferably from 1 to 4 carbon atoms. Representative alcohols include but are not necessarily limited to lower straight and branched chain aliphatic alcohols and their unsaturated counterparts. Examples of suitable oxygenate compounds include, but are not limited to: methanol; ethanol; n-propanol; isopropanol; $C_4$-$C_{20}$ alcohols; methyl ethyl ether; dimethyl ether; diethyl ether; di-isopropyl ether; formaldehyde; dimethyl carbonate; dimethyl ketone; acetic acid; and mixtures thereof. Preferred oxygenate compounds are methanol, dimethyl ether, or a mixture thereof.

Molecular sieves capable of converting an oxygenate to an olefin compound include zeolites as well as non-zeolites, and are of the large, medium or small pore type. Small pore molecular sieves are preferred in one embodiment of this invention, however. As defined herein, small pore molecular sieves have a pore size of less than about 5.0 angstroms. Generally, suitable catalysts have a pore size ranging from about 3.5 to about 5.0 angstroms, preferably from about 4.0 to about 5.0 angstroms, and most preferably from about 4.3 to about 5.0 angstroms.

Zeolite materials, both natural and synthetic, have been demonstrated to have catalytic properties for various types of hydrocarbon conversion processes. In addition, zeolite materials have been used as adsorbents, catalyst carriers for various types of hydrocarbon conversion processes, and other applications. Zeolites are complex crystalline aluminosilicates which form a network of $AlO_2^-$ and $SiO_2$ tetrahedra linked by shared oxygen atoms. The negativity of the tetrahedra is balanced by the inclusion of cations such as alkali or alkaline earth metal ions. In the manufacture of some zeolites, non-metallic cations, such as tetramethylammonium (TMA) or tetrapropylammonium (TPA), are present during synthesis. The interstitial spaces or channels formed by the crystalline network enable zeolites to be used as molecular sieves in separation processes, as catalyst for chemical reactions, and as catalyst carriers in a wide variety of hydrocarbon conversion processes.

Zeolites include materials containing silica and optionally alumina, and materials in which the silica and alumina portions have been replaced in whole or in part with other oxides. For example, germanium oxide, tin oxide, and mixtures thereof can replace the silica portion. Boron oxide, iron oxide, gallium oxide, indium oxide, and mixtures thereof can replace the alumina portion. Unless otherwise specified, the terms "zeolite" and "zeolite material" as used herein, shall mean not only materials containing silicon atoms and, optionally, aluminum atoms in the crystalline lattice structure thereof, but also materials which contain suitable replacement atoms for such silicon and aluminum atoms.

One type of olefin forming catalyst capable of producing large quantities of ethylene and propylene is a silicoaluminophosphate (SAPO) molecular sieve. Silicoaluminophosphate molecular sieves are generally classified as being microporous materials having 8, 10, or 12 membered ring structures. These ring structures can have an average pore size ranging from about 3.5 to about 15 angstroms. Preferred are the small pore SAPO molecular sieves having an average pore size of less than about 5 angstroms, preferably an average pore size ranging from about 3.5 to about 5 angstroms, more preferably from about 3.5 to about 4.2 angstroms. These pore sizes are typical of molecular sieves having 8 membered rings.

According to one embodiment, substituted SAPOs can also be used in oxygenate to olefin reaction processes. These compounds are generally known as MeAPSOs or metal-containing silicoaluminophosphates. The metal can be alkali metal ions (Group IA), alkaline earth metal ions (Group IIA), rare earth ions (Group IIIB, including the lanthanoid elements:lanthanum, cerium, praseodymium, neodymium, samarium, europium, gadolinium, terbium, dysprosium, holmium, erbium, thulium, ytterbium and lutetium; and scandium or yttrium) and the additional transition cations of Groups IVB, VB, VIB, VIIB, VIIIB, and IB.

Preferably, the Me represents atoms such as Zn, Mg, Mn, Co, Ni, Ga, Fe, Ti, Zr, Ge, Sn, and Cr. These atoms can be inserted into the tetrahedral framework through a [MeO$_2$] tetrahedral unit. The [MeO$_2$] tetrahedral unit carries a net electric charge depending on the valence state of the metal substituent. When the metal component has a valence state of +2, +3, +4, +5, or +6, the net electric charge is between −2 and +2. Incorporation of the metal component is typically accomplished adding the metal component during synthesis of the molecular sieve. However, post-synthesis ion exchange can also be used. In post synthesis exchange, the metal component will introduce cations into ion-exchange positions at an open surface of the molecular sieve, not into the framework itself.

Suitable silicoaluminophosphate molecular sieves include SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56, the metal containing forms thereof, and mixtures thereof. Preferred are SAPO-18, SAPO-34, SAPO-35, SAPO-44, and SAPO-47, particularly SAPO-18 and SAPO-34, including the metal containing forms thereof, and mixtures thereof. As used herein, the term mixture is synonymous with combination and is considered a composition of matter having two or more components in varying proportions, regardless of their physical state.

An aluminophosphate (ALPO) molecular sieve can also be included in the catalyst composition. Aluminophosphate molecular sieves are crystalline microporous oxides which can have an $AlPO_4$ framework. They can have additional elements within the framework, typically have uniform pore dimensions ranging from about 3 angstroms to about 10 angstroms, and are capable of making size selective separations of molecular species. More than two dozen structure types have been reported, including zeolite topological analogues. A more detailed description of the background and synthesis of aluminophosphates is found in U.S. Pat. No. 4,310,440, which is incorporated herein by reference in its entirety. Preferred ALPO structures are ALPO-5, ALPO-11, ALPO-18, ALPO-31, ALPO-34, ALPO-36, ALPO-37, and ALPO-46.

The ALPOs can also include a metal substituent in its framework. Preferably, the metal is selected from the group consisting of magnesium, manganese, zinc, cobalt, and mixtures thereof. These materials preferably exhibit adsorption, ion-exchange and/or catalytic properties similar to aluminosilicate, aluminophosphate and silica aluminophosphate molecular sieve compositions. Members of this class and their preparation are described in U.S. Pat. No. 4,567,029, incorporated herein by reference in its entirety.

The metal containing ALPOs have a three-dimensional microporous crystal framework structure of $MO_2$, $AlO_2$ and $PO_2$ tetrahedral units. These as manufactured structures (which contain template prior to calcination) can be represented by empirical chemical composition, on an anhydrous basis, as: $mR: (M_xAl_yP_z)O_2$ wherein "R" represents at least one organic templating agent present in the intracrystalline pore system; "m" represents the moles of "R" present per mole of $(M_xAl_yP_z)O_2$ and has a value of from zero to 0.3, the maximum value in each case depending upon the molecular dimensions of the templating agent and the available void volume of the pore system of the particular metal aluminophosphate involved, "x", "y", and "z" represent the mole fractions of the metal "M", (i.e. magnesium, manganese, zinc and cobalt), aluminum and phosphorus, respectively, present as tetrahedral oxides.

The metal containing ALPOs are sometimes referred to by the acronym as MeAPO. Also in those cases where the metal "Me" in the composition is magnesium, the acronym MAPO is applied to the composition. Similarly ZAPO, MnAPO and CoAPO are applied to the compositions which contain zinc, manganese and cobalt respectively. To identify the various structural species which make up each of the subgeneric classes MAPO, ZAPO, CoAPO and MnAPO, each species is assigned a number and is identified, for example, as ZAPO-5, MAPO-11, CoAPO-34 and so forth.

The silicoaluminophosphate molecular sieve is typically admixed (i.e., blended) with other materials. When blended, the resulting composition is typically referred to as a SAPO catalyst, with the catalyst comprising the SAPO molecular sieve.

Materials which can be blended with the molecular sieve can be various inert or catalytically active materials, or various binder materials. These materials include compositions such as kaolin and other clays, various forms of rare earth metals, metal oxides, other non-zeolite catalyst components, zeolite catalyst components, alumina or alumina sol, titania, zirconia, magnesia, thoria, beryllia, quartz, silica or silica or silica sol, and mixtures thereof. These components are also effective in reducing, inter alia, overall catalyst cost, acting as a thermal sink to assist in heat shielding the catalyst during regeneration, densifying the catalyst and increasing catalyst strength. It is particularly desirable that the inert materials that are used in the catalyst to act as a thermal sink have a heat capacity of from about 0.05 to about 1 cal/g-° C., more preferably from about 0.1 to about 0.8 cal/g-° C., most preferably from about 0.1 to about 0.5 cal/g-° C.

Additional molecular sieve materials can be included as a part of the SAPO catalyst composition or they can be used as separate molecular sieve catalysts in admixture with the SAPO catalyst if desired. Structural types of small pore molecular sieves that are suitable for use in this invention include AEI, AFT, APC, ATN, ATT, ATV, AWW, BIK, CAS, CHA, CHI, DAC, DDR, EDI, ERI, GOO, KFI, LEV, LOV, LTA, MON, PAU, PHI, RHO, ROG, THO, and substituted forms thereof. Structural types of medium pore molecular sieves that are suitable for use in this invention include MFI, MEL, MTW, EUO, MTT, HEU, FER, AFO, AEL, TON, and substituted forms thereof. These small and medium pore molecular sieves are described in greater detail in the *Atlas of zeolite Structural Types*, W. M. Meier and D. H. Olsen, Butterworth Heineman, 3rd ed., 1997, the detailed description of which is explicitly incorporated herein by reference. Preferred molecular sieves which can be combined with a silicoaluminophosphate catalyst include ZSM-5, ZSM-34, erionite, and chabazite.

The catalyst composition, according to an embodiment, preferably comprises from about 1% to about 99%, more preferably from about 5% to about 90%, and most preferably from about 10% to about 80%, by weight of molecular sieve. It is also preferred that the catalyst composition have a particle size of from about 20 angstroms to about 3,000 angstroms, more preferably from about 30 angstroms to about 200 angstroms, most preferably from about 50 angstroms to about 150 angstroms.

The catalyst can be subjected to a variety of treatments to achieve the desired physical and chemical characteristics. Such treatments include, but are not necessarily limited to, hydrothermal treatment, calcination, acid treatment, base treatment, milling, ball milling, grinding, spray drying, and combinations thereof.

A molecular sieve catalyst particularly useful in making ethylene and propylene is a catalyst which contains a combination of SAPO-34, and SAPO-18 or ALPO-18 molecular sieve. In a particular embodiment, the molecular sieve is a crystalline intergrowth of SAPO-34, and SAPO-18 or ALPO-18.

To convert oxygenate to olefin, conventional reactor systems can be used, including fixed bed, fluid bed or moving bed systems. Preferred reactors of one embodiment are cocurrent riser reactors and short contact time, countercurrent free-fall reactors. Desirably, the reactor is one in which an oxygenate feedstock can be contacted with a molecular sieve catalyst at a weight hourly space velocity (WHSV) of at least about 1 $hr^{-1}$, preferably in the range of from about 1 $hr^{-1}$ to 1000 $hr^{-1}$, more preferably in the range of from about 20 $hr^{-1}$ to about 1000 $hr^{-1}$, and most preferably in the range of from about 50 $hr^{-1}$ to about 500 $hr^{-1}$. WHSV is defined herein as the weight of oxygenate, and reactive hydrocarbon which may optionally be in the feed, per hour per weight of the molecular sieve in the reactor. Because the catalyst or the feedstock may contain other materials which act as inerts or diluents, the WHSV is calculated on the weight basis of the oxygenate feed, and any reactive hydrocarbon which may be present with the oxygenate feed, and the molecular sieve contained in the reactor.

Preferably, the oxygenate feed is contacted with the catalyst when the oxygenate is in a vapor phase. Alternately, the process may be carried out in a liquid or a mixed vapor/liquid phase. When the process is carried out in a liquid phase or a mixed vapor/liquid phase, different conversions and selectivities of feed-to-product may result depending upon the catalyst and reaction conditions.

The process can generally be carried out at a wide range of temperatures. An effective operating temperature range can be from about 200° C. to about 700° C., preferably from about 300° C. to about 600° C., more preferably from about 350° C. to about 550° C. At the lower end of the temperature range, the formation of the desired olefin products may become markedly slow with a relatively high content of oxygenated olefin by-products being found in the olefin product. However, the selectivity to ethylene and propylene at reduced temperatures may be increased. At the upper end of the temperature range, the process may not form an optimum amount of ethylene and propylene product, but the conversion of oxygenate feed will generally be high.

Operating pressure also may vary over a wide range, including autogenous pressures. Effective pressures include, but are not necessarily limited to, a total pressure of at least 1 psia (7 kPa), preferably at least about 5 psia (34 kPa). The process is particularly effective at higher total pressures, including a total pressure of at least about 20 psia (138 kPa). Preferably, the total pressure is at least about 25 psia (172 kPa), more preferably at least about 30 psia (207 kPa). For practical design purposes it is desirable to use methanol as the primary oxygenate feed component, and operate the reactor at a pressure of not greater than about 500 psia (3445 kPa), preferably not greater than about 400 psia (2756 kPa), most preferably not greater than about 300 psia (2067 kPa).

Undesirable by-products can be avoided by operating at an appropriate gas superficial velocity. As the gas superficial velocity increases the conversion decreases avoiding undesirable by-products. As used herein, the term, "gas superficial velocity" is defined as the combined volumetric flow rate of vaporized feedstock, which includes diluent when present in the feedstock, as well as conversion products, divided by the cross-sectional area of the reaction zone. Because the oxygenate is converted to a product having significant quantities of ethylene and propylene while flowing through the reaction zone, the gas superficial velocity may vary at different locations within the reaction zone. The degree of variation depends on the total number of moles of gas present and the cross section of a particular location in the reaction zone, temperature, pressure and other relevant reaction parameters.

In one embodiment, the gas superficial velocity is maintained at a rate of greater than 1 meter per second (m/s) at least one point in the reaction zone. In another embodiment, it is desirable that the gas superficial velocity is greater than about 2 m/s at least one point in the reaction zone. More desirably, the gas superficial velocity is greater than about 2.5 n/s at least one point in the reaction zone. Even more desirably, the gas superficial velocity is greater than about 4 m/s at least one point in the reaction zone. Most desirably, the gas superficial velocity is greater than about 8 m/s at least one point in the reaction zone.

According to yet another embodiment of the invention, the gas superficial velocity is maintained relatively constant in the reaction zone such that the gas superficial velocity is maintained at a rate greater than 1 m/s at all points in the reaction zone. It is also desirable that the gas superficial velocity be greater than about 2 m/s at all points in the reaction zone. More desirably, the gas superficial velocity is greater than about 2.5 m/s at all points in the reaction zone. Even more desirably, the gas superficial velocity is greater than about 4 m/s at all points in the reaction zone. Most desirably, the gas superficial velocity is greater than about 8 m/s at all points in the reaction zone.

The amount of ethylene and propylene produced in the oxygenate to olefin process can be increased by reducing the conversion of the oxygenates in the oxygenate to olefins reaction. However, reducing the conversion of feed oxygenates in the oxygenate conversion reaction tends to increase the amount of oxygenated hydrocarbons, particularly including dimethyl ether, that are present in the olefin product. Thus, control of the conversion of feed to the oxygenate reaction process can be important.

According to one embodiment, the conversion of the primary oxygenate, e.g., methanol, is from 90 wt % to 98 wt %. According to another embodiment the conversion of methanol is from 92 wt % to 98 wt %, preferably from 94 wt % to 98 wt %.

According to another embodiment, the conversion of methanol is above 98 wt % to less than 100 wt %. According to another embodiment, the conversion of methanol is from 98.1 wt % to less than 100 wt %; preferably from 98.2 wt % to 99.8 wt %. According to another embodiment, the conversion of methanol is from 98.2 wt % to less than 99.5 wt %; preferably from 98.2 wt % to 99 wt %.

In this invention, weight percent conversion is calculated on a water free basis unless otherwise specified. Weight percent conversion on a water free basis is calculated as: 100× (weight oxygenate fed on a water free basis–weight oxygenated hydrocarbon in the product on a water free basis). The water free basis of oxygenate is calculated by subtracting out the water portion of the oxygenate in the feed and product, and excluding water formed in the product. For example, the weight flow rate of methanol on an oxygenate free basis is calculated by multiplying the weight flow rate of methanol by 14/32 to remove the water component of the methanol. As another example, the rate flow rate of dimethyl ether on an oxygenate free basis is calculated by multiplying the weight flow rate of diemethylether by 28/46 to remove the water component of the dimethyl ether. If there is a mixture of oxygenates in the feed or product, trace oxygenates are not included. When methanol and/or dimethyl ether is used as the feed, only methanol and dimethyl ether are used to calculate conversion on a water free basis.

In this invention, selectivity is also calculated on a water free basis unless otherwise specified. Selectivity is calculated as: 100×wt % component/(100–wt % water–wt % methanol–wt % dimethyl ether) when methanol and/or dimethyl ether is used as the feed.

The greater the amount of dimethyl ether in the olefin product of an oxygenate to olefin reaction, the lower the percent conversion. Since it is desirable to run the reaction at lower conversion in order to increase selectivity to ethylene and propylene, it is desirable to have some quantity of dimethyl ether in the olefin produced. However, the amount of dimethyl ether present should not be so high to make the overall process inefficient or the removal of dimethyl ether more difficult.

Desirably, the dimethyl ether will be present in the olefin produced in an oxygenate to olefin reaction process in an amount of at least about 100 ppm by weight on a water free basis. Preferably, the dimethyl ether is present in an amount of at least about 500 ppm by weight, and more preferably at least about 1000 ppm by weight. Preferably, the amount of dimethyl ether in the olefin stream from the oxygenate to olefin reaction process, on a water free basis, is not greater than about 10 wt %, more preferably not greater than about 5 wt %, and most preferably not greater than about 2 wt %.

The oxygenate to olefin process forms a substantial amount of water as a by-product. Much of this water by-product can be removed prior to distillation by cooling the stream to a temperature below the condensation temperature of the water vapor in the stream. Preferably, the temperature of the product stream is cooled to a temperature below the condensation temperature of the oxygenate feed. In certain embodiments it is desirable to cool the product stream below the condensation temperature of methanol.

It is desirable to cool the olefin stream from the oxygenate to olefin reaction process, then separate the cooled olefin stream into a condensed, water containing stream and an olefin vapor stream. The condensed, water containing stream comprises most of the water from the olefin stream, and a significant portion of the oxygenated hydrocarbons from the olefin stream. The olefin vapor stream comprises a majority of the olefins, e.g., ethylene and propylene.

In one aspect of the invention, the olefin stream from the oxygenate to olefin reaction process is cooled so that a vapor stream, rich in olefins, can be separated from the condensed water containing stream. It is desirable that the vapor stream contain not greater than about 20 wt % water, preferably not greater than about 15 wt % water, more preferably not greater than about 12 wt % water.

A quench column is one type of equipment that is effective in cooling the olefin stream from the olefin to oxygenate reaction process. In a quench column, a quenching fluid is directly contacted with the olefin stream to cool the stream to the desired condensation temperature. Condensation produces the condensed water containing stream, which is also referred to as a heavy bottoms stream. The olefin portion of the olefin product stream remains a vapor, and exits the quench column as an overhead vapor stream. The overhead vapor stream is rich in olefin product, and can also contain some oxygenated hydrocarbon by-products as well as water.

In one embodiment, the quenching fluid is a recycle stream of the condensed water containing, heavy bottoms stream of the quench column. This water containing stream is desirably cooled, e.g., by a heat exchanger, and injected back into the quench column. It is preferred in this embodiment to not inject cooling medium from an outside source into the quench column, although it may be desirable to do so in other separation equipment down stream of the quench column.

In one embodiment of the invention, the olefin stream containing the dimethyl ether is dried before the propane and dimethyl ether stream is separated out. In this embodiment, a solid or liquid drying system can be used to remove water from the olefin stream containing the dimethyl ether (i.e., dry the olefin stream) prior to distillation to more effectively remove the dimethyl ether.

In the solid drying system, the olefin stream is contacted with a solid adsorbent to further remove water to very low levels. Any conventional method can be used. Typically, the adsorption process is carried out in one or more fixed beds containing a suitable solid adsorbent.

Adsorption is useful for removing low concentrations of water, as well as for removing certain oxygenated hydrocarbons that may not normally be removed by using other treatment systems. Preferably, an adsorbent system used as part of this invention has multiple adsorbent beds. Multiple beds allow for continuous separation without the need for shutting down the process to regenerate the solid adsorbent. For example, in a three bed system typically one bed is on-line, one bed is regenerated off-line, and a third bed is on stand-by.

The specific adsorbent solid or solids used in the adsorbent beds depends on the types of contaminants being removed. Examples of solid adsorbents for removing water and various polar organic compounds, such as oxygenated hydrocarbons and absorbent liquids, include aluminas, silica, molecular sieves, and alumino-silicates. Beds containing mixtures of these sieves or multiple beds having different adsorbent solids can be effectively used to remove water to very low levels.

The adsorbent beds can be operated at ambient temperature or at elevated temperature as required, and with either upward or downward flow. Regeneration of the adsorbent materials can be carried out by conventional methods including treatment with a stream of a dry inert gas such as nitrogen at elevated temperature.

In the liquid drying system, a water absorbent is used to remove water from the olefin stream containing the dimethyl ether. The water absorbent can be any liquid effective in removing water from an olefin stream. The amount of water absorbent to be used is an amount effective in substantially reducing clathrate and free water formation during the distillation process.

It is preferred that water absorbent be added to a water absorption vessel at a molar ratio of water absorbent to total feed entering the absorption vessel of about 1:1 to about 1:5,000, more preferably from about 1:10 to about 1:1,000, and most preferably from about 1:25 to about 1:500.

Water absorbents which can be used in this invention are liquids at 1 atm. These absorbents also desirably have an average boiling point of at least 100° F. (38° C.), preferably at least 120° F. (49° C.), and more preferably at least 150° F. (66° C.). Average boiling point, as defined herein, takes into account the boiling point of each compound in the absorbent on a weight average basis. For example, an absorbent containing 90 wt. % of a compound having a boiling point of 100 degrees and 10 wt. % of a compound having a boiling point of 200 degrees would have an average boiling point of 110 degrees.

The water absorbents are also desirably polar hydrocarbon compositions. Such compositions preferably contain compounds such as monohydric alcohols, polyhydric alcohols, amines, or mixtures thereof. Preferred monohydric alcohols include methanol, ethanol and propanol. Preferred polyhydric alcohols include glycols. Preferred glycols include ethylene glycol and tri-ethylene glycol. It is desirable that the absorbent composition contain at least about 75 wt. % liquid water absorbent. The remainder of the composition can be a diluent as long as the diluent does not adversely impact water absorption. Preferably, the water absorbent composition contains at least about 85 wt. % of a water absorbing compound; more preferably at least about 90 wt. %, and most preferably at least about 95 wt. %. Methanol is most preferred as the water absorbent.

Conventional absorption systems can be used in this invention to contact absorbent with olefin. In one embodiment, the absorption system uses packed columns, although plate absorption columns may also be used. In another embodiment, the absorption column has a liquid inlet located at a top portion of the absorption column. The absorbent liquid is evenly distributed across the top of the column. Desirably, an even distribution of the absorbent liquid is accomplished by using a distributor plate or spray nozzles. At the bottom of the absorption column is a gas inlet where the olefin, containing water and dimethyl ether, enters the absorption column. The vapor components move up the column countercurrent to the liquid absorbent moving down the column. This is known as countercurrent absorption.

The packing or plates in the column provides a surface for intimate contact between the vapor and liquid components within the column. In a countercurrent absorption column, the concentration of soluble gasses in both the liquid and vapor phases is greatest at the bottom of the column, and lowest at the top of the column. The outlet for the vapor is at the bottom of the absorption column, typically below the gas inlet. The outlet for the gas phase lean in the gasses most soluble in the liquid absorbent is at the top of the absorption column, typically above the liquid inlet.

One or more absorption columns can be used in series or in parallel to decrease the concentration of water to desired levels, and to handle larger volumes of olefin composition from the oxygenate to olefin process. Following absorption, the olefin stream can be distilled to remove a propane and dimethyl ether stream.

Absorbent liquid can be regenerated by conventional means. In one embodiment, the absorbent liquid containing the absorbed gasses is fed into a distillation column, and water is removed as an overhead product. Regenerated absorbent liquid is removed as a bottoms product.

In another embodiment of the invention, the quenched and/or dried olefin stream can be further processed by compression, preferably multi-staged compression. Two, three, four or more stages can be used, with two or three stages being preferred.

Desirably, the quenched and/or dried olefin stream is compressed to a pressure that is greater than that at which the oxygenate to olefin reaction process is carried out. Preferably, the olefin stream is compressed to a pressure of at least about 30 psia (207 kPa), more preferably at least about 50 psia (345 kPa), most preferably at least about 100 psia (689 kPa). High pressure ranges are particularly preferred, with the upper limit being a practical one based on cost of design and ease of operation. Practical high pressure limits are generally considered to be up to about 5,000 psia (34,450 kPa), with lower limits of about 1,000 psia (6,895 kPa), about 750 psia (5171 kPa), and about 500 psia (3447 kPa) being increasingly preferred.

Conventional distillation techniques can be used in this invention. In one embodiment of the invention, the separation of the propane and dimethyl ether stream from the olefin stream takes place in a distillation type of column and the operation pressure of the column is held so that the bottoms portion of the column is at a relatively low temperature so as to limit equipment fouling. This bottoms fraction will contain a majority of the $C_4$+ olefin components from the olefin feed. In this embodiment, it is preferred that the bottoms fraction have an average temperature of not greater than about 300° F. (149° C.), more preferably not greater than about 275° F. (135° C.), and most preferably not greater than about 250° F. (121° C.).

In this invention, it is desirable to conduct distillation at a temperature which will allow for fractionation of the olefin feedstream between the boiling point of propylene and propane. Separating the propane out in this manner will result in a stream which contains the propane plus the dimethyl ether contained in the olefin stream. The lighter boiling point olefin compounds, e.g., ethylene and propylene, are then further distilled to obtain separate ethylene and propylene streams. These streams will be substantially polymer grade feed quality, containing not greater than about 10 wppm dimethyl ether, preferably not greater than about 5 wppm dimethyl ether, more preferably not greater than about 1 wppm dimethyl ether.

In this invention, the olefin stream containing the dimethyl ether is distilled so as to separate out a propane and dimethyl ether containing stream from the other components of the olefin stream. Preferably, the olefin stream containing the dimethyl ether is distilled so as to separate a propane and dimethyl ether stream from the olefin stream which contains from about 4 wt % to about 99 wt % propane; more preferably from about 10 wt % to about 85 wt % propane; and most preferably from about 15 wt % to about 90 wt % propane. The propane and dimethyl ether stream also contains dimethyl ether at an amount of from about 1 wt % to about 96 wt %; preferably from about 15 wt % to about 90 wt %; and more preferably from about 20 wt % to about 85 wt %. The relative amount of propane and dimethyl ether in the stream can vary when olefins from an oxygenate to olefins conversion process is used, due to the desired conversion of oxygenate to olefin. The conversion of oxygenate to olefin is desirably from about 95% to about 99%.

In another embodiment of the invention, an ethylene and/or propylene stream is recovered following distillation. The ethylene and/or propylene stream is substantially free of dimethyl ether, substantially free meaning substantially low in dimethyl ether concentration so as not to substantially adversely affect downstream processing of ethylene and propylene. Preferably, the separated ethylene and/or propylene stream will contain not greater than about 25 wppm, preferably not greater than about 10 wppm, more preferably not greater than about 6 or 3 or 1 wppm dimethyl ether, and most preferably not greater than about 0.5 wppm dimethyl ether.

In another embodiment, at least about 75% of the dimethyl ether in the olefin stream containing the dimethyl ether will be separated out in distillation. Preferably, at least about 85% of the dimethyl ether in the olefin stream will be separated out in distillation, more preferably at least about 95%, and most preferably at least about 99%.

Examples of distilling an olefin stream to separate out a propane and dimethyl ether stream according to this invention are shown in FIGS. 1-5. These examples demonstrate that there are numerous ways of distilling olefin streams, depending upon the starting feed quality and the flow path chosen. However, the common factor in this invention is the separation of dimethyl ether along with the propane component of the olefin stream using conventional distillation techniques.

Figure 1:
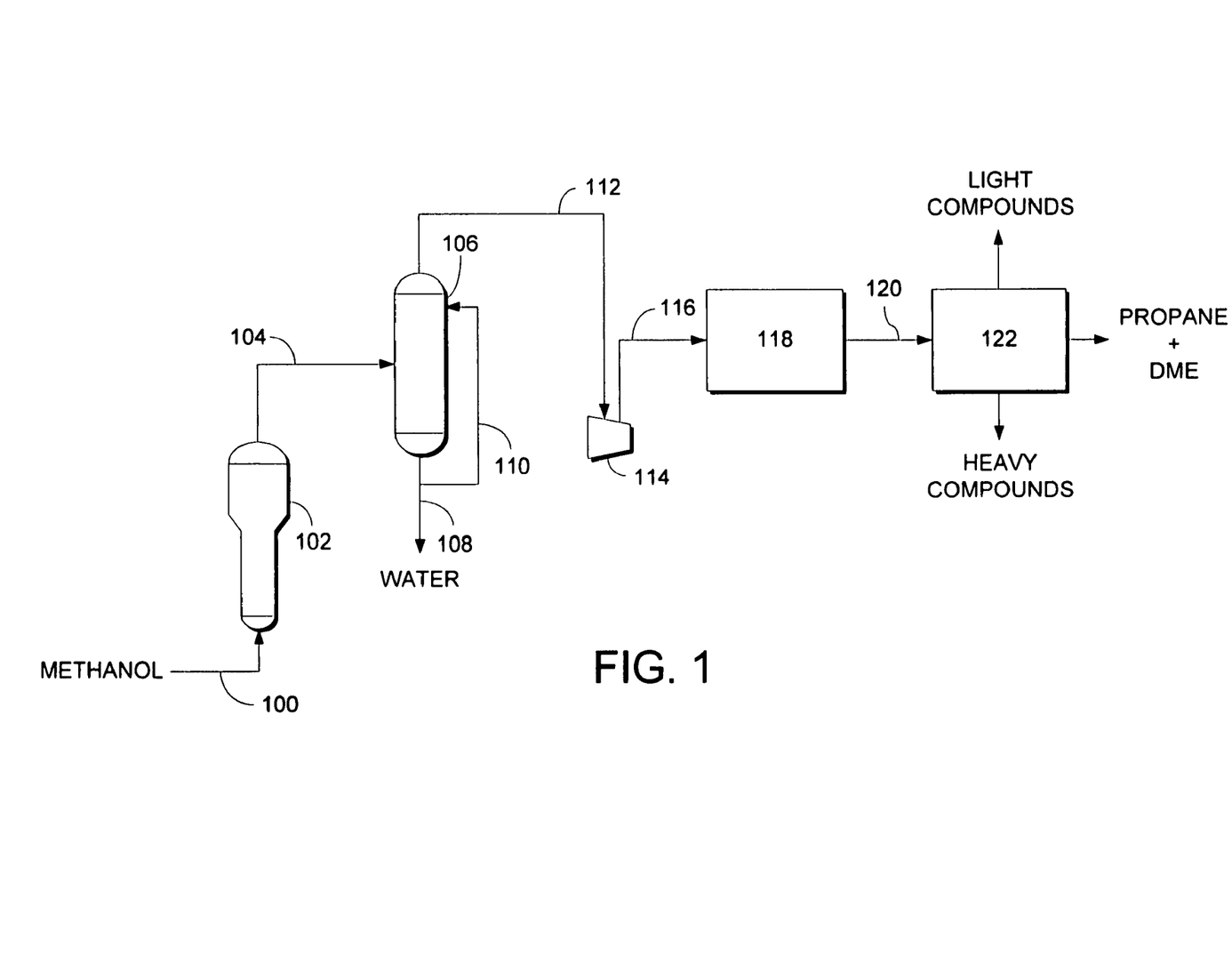
FIG. 1 is a flow diagram showing making an olefin from an oxygenate, drying the olefin, and separating a propane and dimethyl ether stream from the dried olefin.

FIG. 1 is a flow diagram showing making an olefin from an oxygenate, drying the olefin, and separating a propane and dimethyl ether stream from the dried olefin. Methanol is used as the oxygenate, and the methanol is sent through a line 100 to an oxygenate to olefin reactor 102 where the methanol is converted to an olefin stream comprising methane, ethylene, propylene, acetaldehyde, $C_4+$ olefins, water and other hydrocarbon components. The olefin stream is sent through a line 104 to a quench tower 106 where the olefin is cooled and water and other condensable components are condensed.

The condensed components, which comprise a substantial amount of water, are withdrawn from the quench tower 106 through a bottoms line 108. A portion of the condensed components are recycled through a line 110 back to the top of the quench tower 106. The line 110 contains a cooling unit, e.g., heat exchanger, (not shown) to further cool the condensed components so as to provide a cooling medium to further cool the components in quench tower 106.

Olefin vapor leaves the top portion of quench tower 106 through a line 112. The olefin vapor is compressed in compressor 114 and the compressed olefin is passed through a line 116 to a drying unit 118 to remove additional water from the olefin vapor. The dried olefin is sent through a line 120 to a distillation unit 122. The distillation unit is operated to separate light and heavy components from a propane and dimethyl ether (DME) stream. Included in the light components is ethylene and/or propylene which can be sent on for further processing such as polymerization or other derivative processing. The dimethyl ether is separated from the propane by water washing, and the separated dimethyl ether is recycled to the olefin reactor to contact molecular sieve catalyst in the olefin reactor to form additional olefin (not shown).

Figure 2:
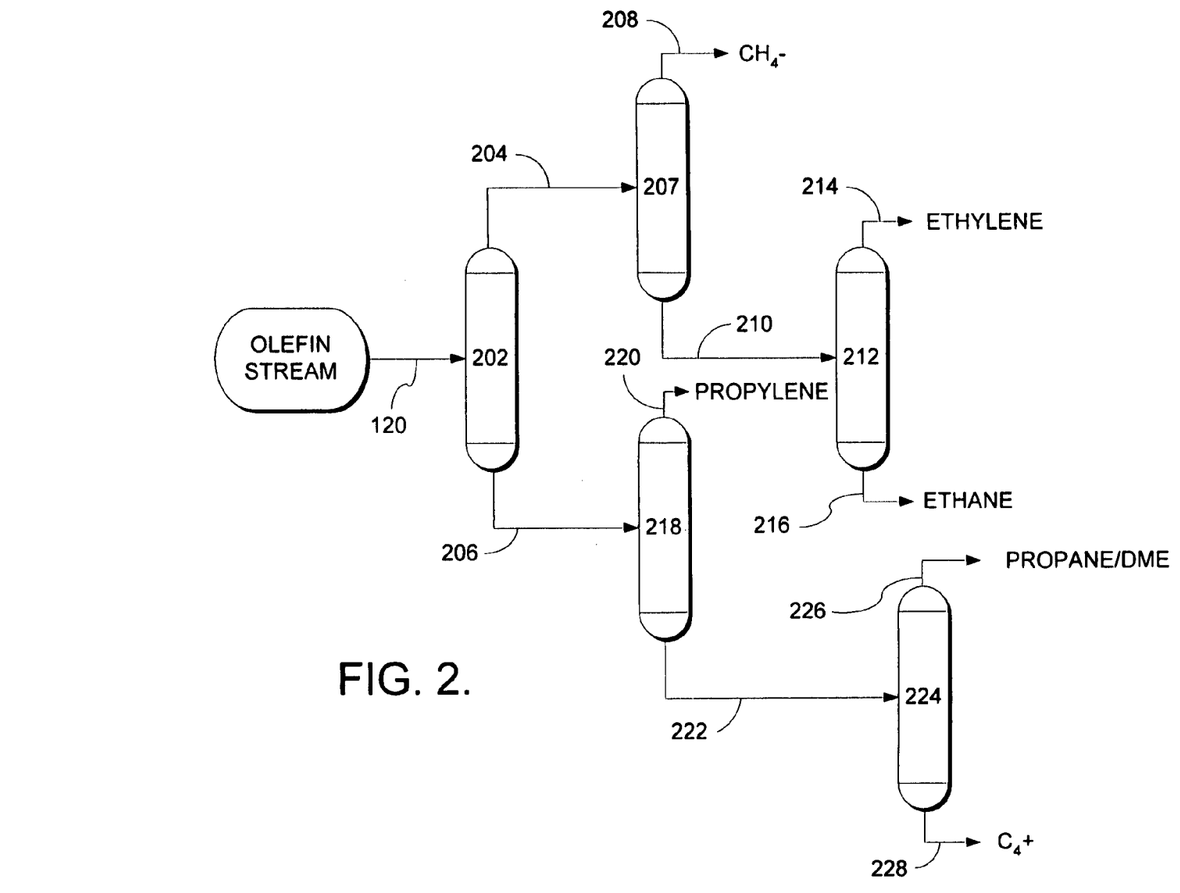
FIG. 2 is a flow diagram of a deethanizer first fractionation embodiment of this invention.

FIG. 2 shows a deethanizer first embodiment. In FIG. 2, an olefin stream 120 that comprises ethane, ethylene, propane, propylene, dimethyl ether, and $C_4+$ olefins and other hydrocarbons is fed to deethanizer column 202. Deethanizer column 202 fractionates or distills olefin stream 120 to produce an overhead stream 204 comprising ethane, ethylene and lighter boiling point components and a bottoms stream 206 comprising propylene, propane, dimethyl ether and $C_4+$ olefins and other hydrocarbons. The overhead stream 204 is fed to demethanizer column 207. Demethanizer column 207 produces an overhead stream 208 comprising methane and lighter boiling point components and a bottoms stream 210 comprising ethane and ethylene. Bottoms stream 210 is fed into $C_2$ splitter 212. $C_2$ splitter 212 produces an overhead stream 214 comprising ethylene and a bottoms stream 216 comprising ethane. The bottoms stream 206 from the deethanizer 202 is fed to $C_3$ splitter 218. The $C_3$ splitter fractionates or distills bottoms stream 206 to produce an overhead stream 220 comprising propylene and a bottoms stream 222 comprising propane, dimethyl ether, and $C_4+$ olefins and other hydrocarbons. The bottoms stream 222 is fed to a distillation column 224. The distillation column 224 fractionates or distillation bottoms stream 222 to produce an overhead stream 226 comprising propane and dimethyl ether, and a bottoms stream 228 comprising $C_4+$ olefins and other hydrocarbons.

Figure 3:
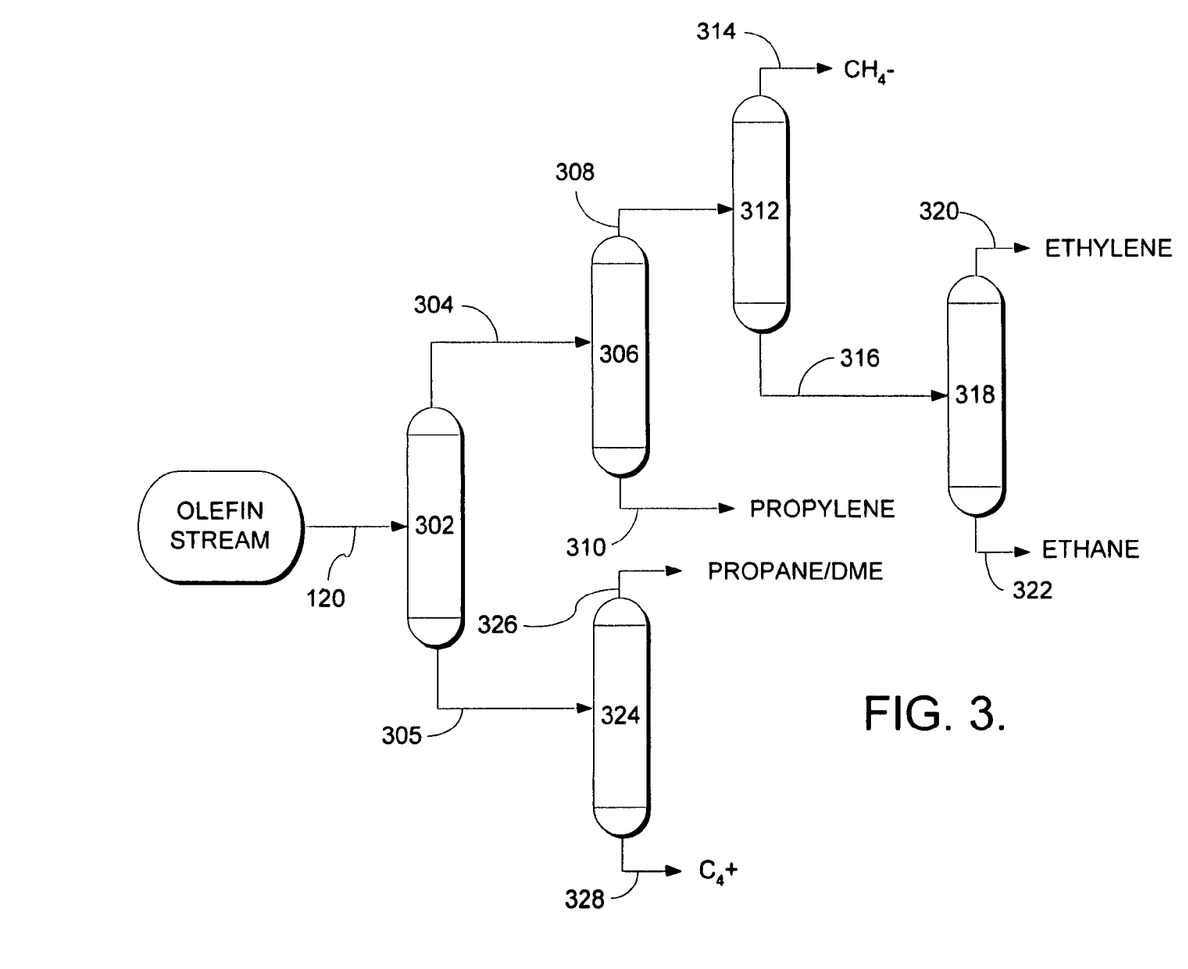
FIG. 3 is a flow diagram of a $C_3$ splitter first fractionation embodiment of this invention.

FIG. 3 is a $C_3$ splitter first fractionation or distillation embodiment. In FIG. 3, olefin stream 120 is first fed to $C_3$ splitter 302 to produce an overhead stream 304 comprising propylene, ethane, ethylene, and lighter boiling point compounds and a bottoms stream 305 comprising propane, dimethyl ether, and $C_4+$ olefins and other hydrocarbons. Overhead stream 304 is fed to deethanizer column 306 to produce an overhead stream 308 which comprises ethane, ethylene, and lighter boiling point compounds and a bottoms stream 310 which comprises propylene. Overhead stream 308 is fed to demethanizer 312 to produce an overhead stream 314 comprising methane and lighter boiling point components and a bottoms stream 316 comprising ethane and ethylene. The bottoms stream 316 is fed to $C_2$ splitter 318 to produce an overhead stream 320 comprising ethylene and a bottoms stream 322 comprising ethane. The bottoms stream from the $C_3$ splitter 302 is fed to distillation column 324 to produce an overhead stream 326 comprising propane and dimethyl ether, and a bottoms stream 328 comprising $C_4+$ olefins and other hydrocarbons.

Figure 4:
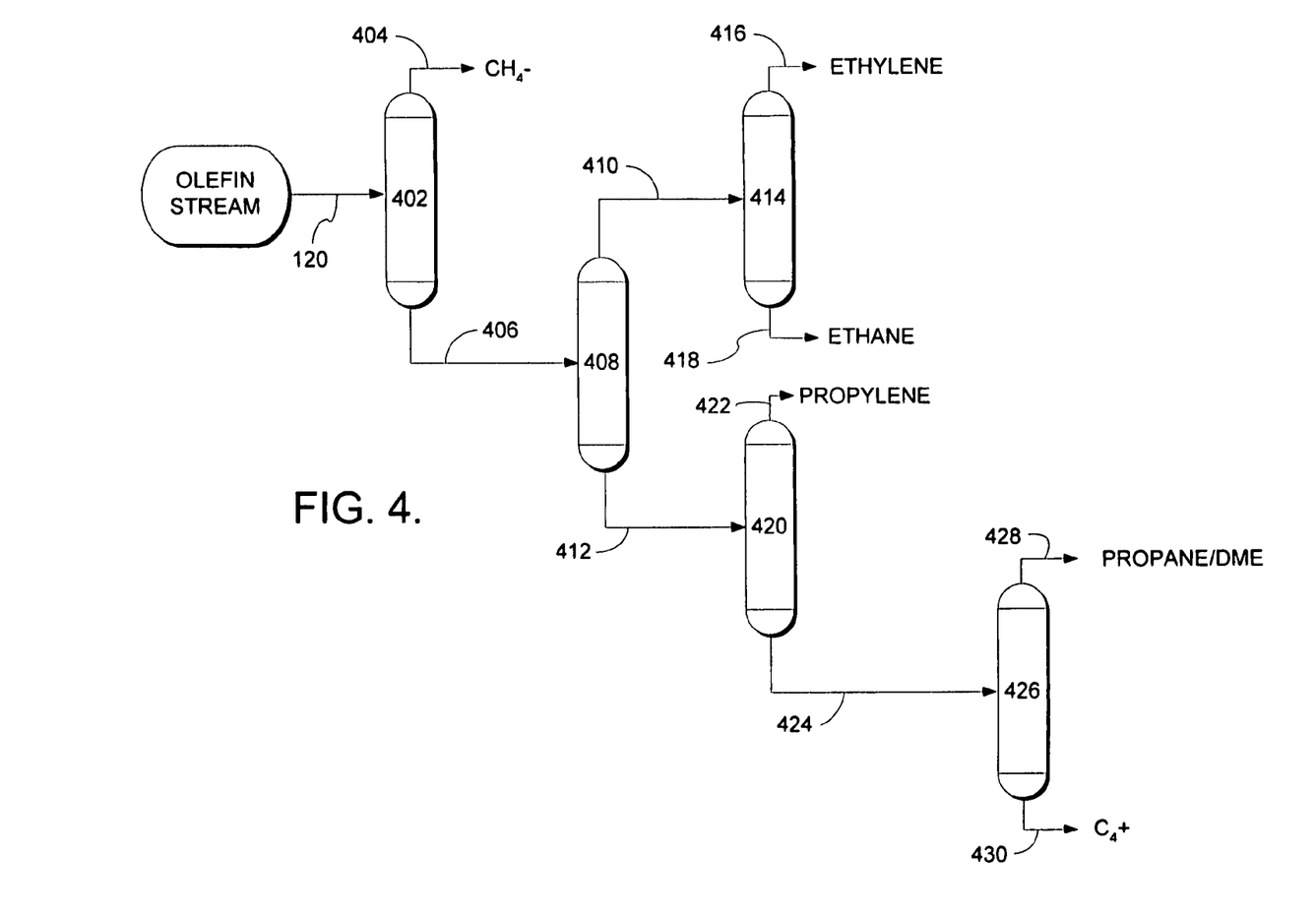
FIG. 4 is a flow diagram of a demethanizer to deethanizer first fractionation embodiment of this invention.

FIG. 4 is a demethanizer to deethanizer first fractionation embodiment. In FIG. 4, olefin stream 120 is fed to demethanizer column 402 to produce an overhead 404 comprising methane and lighter boiling point compounds and a bottoms stream 406 comprising ethane, ethylene, propane, propylene, dimethyl ether and $C_4+$ hydrocarbons. The bottoms stream 406 is fed to deethanizer column 408 to produce an overhead stream 410 comprising ethane and ethylene and a bottoms stream 412 comprising propylene, propane, dimethyl ether and $C_4+$ olefins and other hydrocarbons. The overhead stream 410 is fed to a $C_2$ splitter to produce an overhead stream 416 an ethylene feed stream and a bottoms stream 418 comprising ethane. The bottoms stream 412 is fed into $C_3$ splitter 420 to produce an overhead stream 422 comprising propylene and a bottoms stream 424 comprising propane, dimethyl ether, and $C_4+$ olefins and other hydrocarbons. Bottoms stream 424 is fed to distillation column 426 to produce an overhead stream 428 comprising propane and dimethyl ether, and a bottoms stream 430 comprising $C_4+$ olefins and other hydrocarbons.

Figure 5:
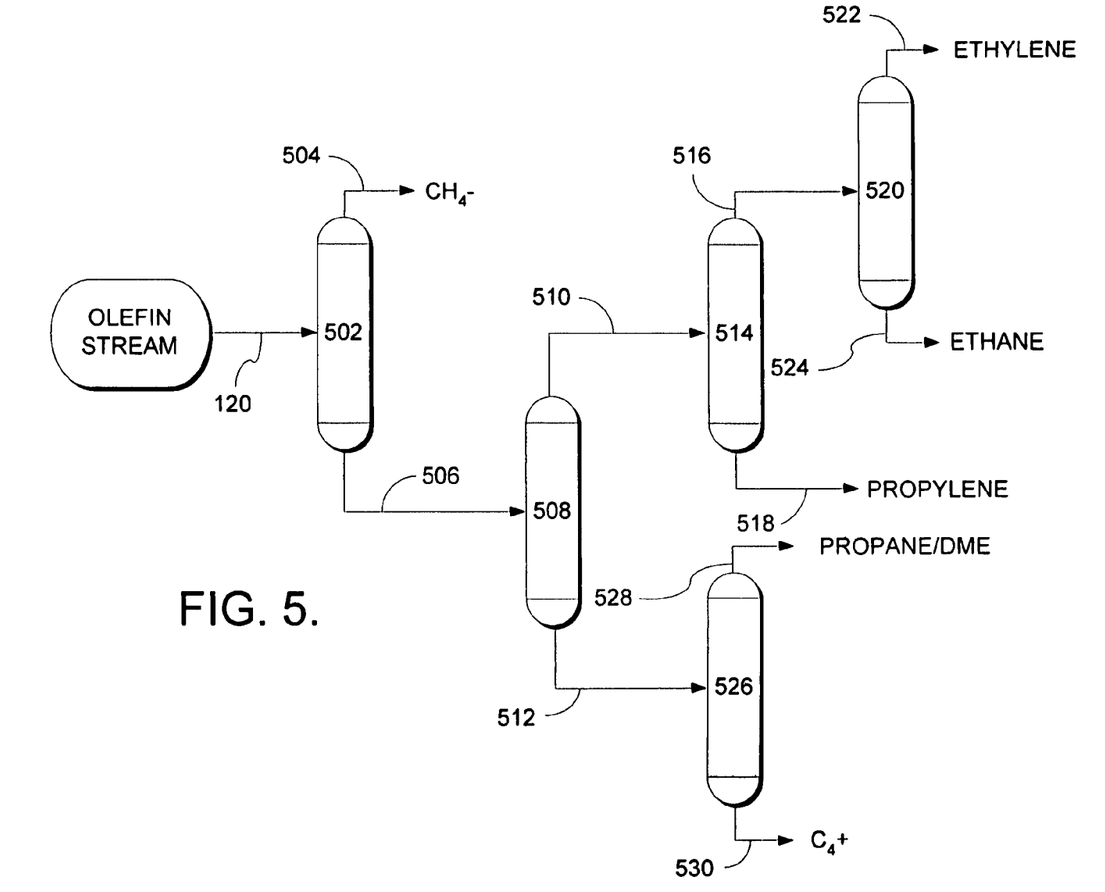
FIG. 5 is a flow diagram of a demethanizer first fractionation embodiment of this invention.

FIG. 5 is a demethanizer to $C_3$ splitter first fractionation embodiment. In FIG. 5, olefin stream 120 is fed to demethanizer column 502 to produce an overhead stream 504 comprising methane and lighter boiling point compounds and a bottoms stream 506 comprising ethane, ethylene, propane, propylene, dimethyl ether and $C_4+$ olefins and other hydrocarbons. Bottoms stream 506 from the demethanizer column is fed into $C_3$ splitter 508 to produce an overhead stream 510 comprising propylene, ethane, and ethylene and a bottoms stream 512 comprising propane, dimethyl ether, and $C_4+$ olefins and other hydrocarbons. Overhead stream 510 is fed into deethanizer column 514 to produce an overhead stream 516 comprising ethane and ethylene and a bottoms stream 518 comprising propylene. The overhead stream 516 is fed to $C_2$ splitter 520 to produce an overhead stream 522 comprising ethylene and a bottoms stream 524 comprising ethane. Bottoms stream 512 from the $C_3$ splitter is fed to distillation column 526 to produce an overhead stream 528 comprising propane and dimethyl ether, and a bottoms stream 530 comprising $C_4+$ olefins and other hydrocarbons.

Figure 6:
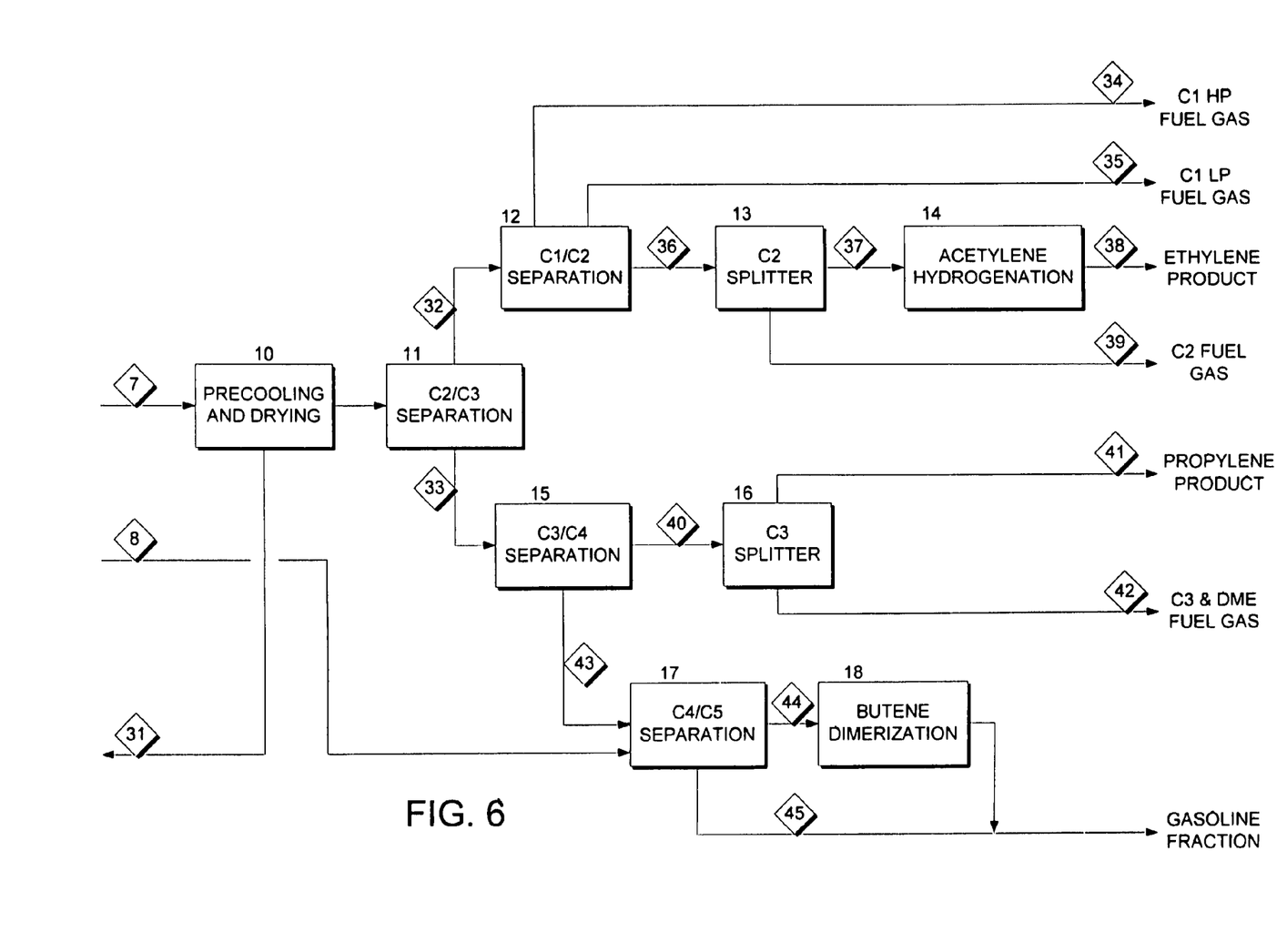
FIG. 6 is a flow diagram of a deethanizer first fractionation embodiment of this invention.

FIG. 6 shows another type of deethanizer first embodiment of the invention. According to FIG. 6, an olefin-containing product stream from a reactor for olefin synthesis from methanol (not shown in the Figure) is sent via a pipe (7) to a precooling and drying step (10). Accumulated condensate (predominantly water) is removed through a pipe (31). The precooled and dried product stream is then sent to a $C_2/C_3$ separation step (11). $C_1/C_2$ hydrocarbons are separated and sent through a pipe (32) to a $C_1/C_2$ separation step (12). The separated $C_1$ hydrocarbons are recovered as a high pressure (HP) and low pressure (LP) fuel gas through pipes (34) and (35). The separated $C_2$ hydrocarbons are sent through a pipe (36) to a $C_2$ splitter (13).

In the $C_2$ splitter, ethylene is separated from ethane and removed through a pipe (37). The ethylene, which can contain some acetylene, is sent to an acetylene hydrogenation step (14) and recovered as ethylene product (38) through a pipe (39). $C_2$ combustion gas (predominantly ethane) is withdrawn from the $C_2$ splitter and sent through a pipe (39).

The $C_3+$ hydrocarbons (i.e., hydrocarbons that have a boiling point greater than or equal to propylene) that are separated from the olefin stream in the $C_2/C_3$ separation step (11) are sent through pipe (33) to a $C_3/C_4$ separation step (15), where separation of the $C_3$ hydrocarbons from the heavier hydrocarbons (i.e., $C_4+$ hydrocarbons) takes place. The heavier $C_4+$ hydrocarbons are sent through a pipe (43) to a $C_4/C_5$ separation step (17). The $C_5+$ hydrocarbons are separated from the $C_4$ hydrocarbons, and ultimately sent through a line (45) for use as a gasoline fraction. The $C_4$ hydrocarbons are separated and sent through a line (44) to a butene dimerization step (18) to form dimerized hydrocarbons. The dimerized hydrocarbons are also ultimately sent through the line (45) for use as a gasoline fraction.

The $C_3$ hydrocarbons that are separated at the $C_3/C_4$ separation step (15), are sent through a pipe (40) to a $C_3$ splitter (16). Dimethyl ether, which is present in the olefin stream, also goes to the $C_3$ splitter along with the $C_3$ hydrocarbons, since it behaves like propane in the preceding fractionation steps. In the $C_3$ splitter (16), the dimethyl ether, together with the propane, goes to the bottom of the splitter, and both are removed through a pipe (42). Substantially pure propylene product, e.g., containing less than 3 ppm dimethyl ether, is obtained from the top of the $C_3$ splitter (16) through a pipe (41).

The ethylene and propylene streams separated according to this invention can be polymerized to form plastic compositions, e.g., polyolefins, particularly polyethylene and polypropylene. Any conventional process for forming polyethylene or polypropylene can be used. Catalytic processes are preferred. Particularly preferred are metallocene, Ziegler/Natta, chromium oxide and acid catalytic systems. See, for example, U.S. Pat. Nos. 3,258,455; 3,305,538; 3,364,190; 5,892,079; 4,659,685; 4,076,698; 3,645,992; 4,302,565; and 4,243,691, the catalyst and process descriptions of each being expressly incorporated herein by reference. In general, these methods involve contacting the ethylene or propylene product with a polyolefin-forming catalyst at a pressure and temperature effective to form the polyolefin product.

In one embodiment of this invention, the ethylene or propylene product is contacted with a metallocene catalyst to form a polyolefin. Desirably, the polyolefin forming process is carried out at a temperature ranging between about 50° C. and about 320° C. The reaction can be carried out at low, medium or high pressure, being anywhere within the range of about 1 bar to about 3200 bar. For processes carried out in solution, an inert diluent can be used. In this type of operation, it is desirable that the pressure be at a range of from about 10 bar to about 150 bar, and preferably at a temperature range of from about 120° C. to about 250° C. For gas phase processes, it is preferred that the temperature generally be within a range of about 60° C. to 120° C., and that the operating pressure be from about 5 bar to about 50 bar.

In addition to polyolefins, numerous other olefin derivatives may be formed from the ethylene, propylene and $C_4+$ olefins, particularly butylene, separated according to this invention. The olefins separated according to this invention can also be used in the manufacture of such compounds as aldehydes, acids such as $C_2$-$C_{13}$ mono carboxylic acids, alcohols such as $C_2$-$C_{12}$ mono alcohols, esters made from the $C_2$-$C_{12}$ mono carboxylic acids and the $C_2$-$C_{12}$ mono alcohols, linear alpha olefins, vinyl acetate, ethylene dicholoride and vinyl chloride, ethylbenzene, ethylene oxide, cumene, acrolein, allyl chloride, propylene oxide, acrylic acid, ethylene-propylene rubbers, and acrylonitrile, and trimers and dimers of ethylene and propylene. The $C_4+$ olefins, butylene in particular, are particularly suited for the manufacture of aldehydes, acids, alcohols, esters made from $C_5$-$C_{13}$ mono carboxylic acids and $C_5$-$C_{13}$ mono alcohols and linear alpha olefins.

Having now fully described this invention, it will be appreciated by those skilled in the art that the invention can be performed within a wide range of parameters within what is claimed, without departing from the spirit and scope of the invention.

The invention claimed is:

1. A method of separating dimethyl ether from an olefin stream made from an oxygenate to olefin reaction process, comprising:

contacting oxygenate with a molecular sieve catalyst to form the olefin stream, wherein the olefin stream comprises water, propylene, propane, and dimethyl ether;

drying the olefin stream; and distilling the dried olefin stream to separate the dimethyl ether and propane as a bottoms from the propylene wherein the dried olefin stream contains not greater than 1,000 wppm water.

2. The method of claim 1, wherein the dried olefin stream contains not greater than 500 wppm water.

3. The method of claim 2, wherein the dried olefin stream contains not greater than 10 wppm water.

4. The method of claim 1, wherein the propylene distilled from the dried olefin stream is substantially free of dimethyl ether.

5. The method of claim 1, wherein the propylene distilled from the dried olefin stream contains not greater than 25 wppm dimethyl ether.

6. The method of claim 5, wherein the propylene distilled from the dried olefin stream contains not greater than 10 wppm dimethyl ether.

7. The method of claim 6, wherein the propylene distilled from the dried olefin stream contains not greater than 1 wppm dimethyl ether.

8. The method of claim 7, wherein the propylene distilled from the dried olefin stream contains not greater than 0.5 wppm dimethyl ether.

9. The method of claim 1, wherein the olefin stream contains at least 0.05 wt % dimethyl ether.

10. The method of claim 1, wherein the olefin stream further comprises butylene and higher boiling point compounds and the dried olefin stream is distilled to separate the dimethyl ether and propane from the propylene, butylene and higher boiling point compounds.

11. The method of claim 1, further comprising contacting the propane and dimethyl ether with water to separate the dimethyl ether from the propane.

12. The method of claim 10, further comprising contacting the separated dimethyl ether with a molecular sieve catalyst to form an olefin.

13. The method of claim 10, wherein the olefin stream comprises from 2 wt % to 45% propane, from 0.05 to 5 wt % dimethyl ether, and from 30 wt % to 95 wt % butylene plus higher boiling point compounds.

14. The method of claim 1, further comprising polymerizing the separated propylene to form polypropylene.

15. The method of claim 10, further comprising separating the butylene and higher boiling point compounds from the propylene.

16. The method of claim 15, further comprising converting the separated butylene into aldehydes, acids, alcohols, esters made from $C_5$-$C_{13}$ mono carboxylic acids and $C_5$-$C_{13}$ mono alcohols or linear alpha olefins.

17. The method of claim 1, wherein the olefin stream further comprises ethylene and the dried olefin stream is distilled to separate the dimethyl ether and propane from the ethylene and propylene.

18. The method of claim 17, further comprising polymerizing the separated ethylene.

19. A method of removing dimethyl ether from an olefin stream, comprising:
    providing an olefin stream which comprises water, propylene, propane and dimethyl ether; drying the olefin stream;
    distilling the dried olefin stream so as to separate out the propane and dimethyl ether as a bottoms from the propylene, wherein the propane and dimethyl ether stream comprises from 4.0 to 99 wt % propane and from 1.0 to 96 wt % dimethyl ether wherein the dried olefin stream contains not greater than 1,000 wppm water.

20. The method of claim 19, wherein the provided olefin stream comprises at least 0.05 wt % dimethyl ether.

21. The method of claim 19, wherein the olefin stream is dried by contacting the olefin stream with water absorbent.

22. The method of claim 21, wherein the water absorbent is a polar hydrocarbon.

23. The method of claim 19, wherein the olefin stream is dried by contacting the olefin stream with a water adsorbent.

24. The method of claim 23, wherein the water adsorbent is a molecular sieve.

25. The method of claim 21, wherein the provided olefin stream is compressed prior to contacting with water absorbent.

26. The method of claim 19, further comprising contacting the propane and dimethyl ether stream with water so as to separate the dimethyl ether from the propane.

27. The method of claim 26, further comprising contacting the separated dimethyl ether with a molecular sieve catalyst to form an olefin.

28. The method of claim 19, further comprising polymerizing the separated propylene.

29. The method of claim 19, wherein the olefin stream further comprises ethylene and the dried olefin stream is distilled to separate the dimethyl ether and propane from the ethylene and propylene.

30. The method of claim 29, further comprising polymerizing the separated ethylene.

\* \* \* \* \*